United States Patent [19]

Lavie

[11] Patent Number: 4,716,046
[45] Date of Patent: * Dec. 29, 1987

[54] PULVERULENT WATER-SOLUBLE NONHYGROSCOPIC COMPOSITION FOR PREPARING BEVERAGES WITH A LASTING EFFERVESCENCE AND METHOD FOR PREPARING THE SAME

[75] Inventor: Louis F. Lavie, Lausanne, Switzerland

[73] Assignee: Dridrinks N.V., Curacao, Netherlands Antilles

[ * ] Notice: The portion of the term of this patent subsequent to Apr. 1, 2003 has been disclaimed.

[21] Appl. No.: 689,440

[22] Filed: Jan. 7, 1985

Related U.S. Application Data

[63] Continuation-in-part of Ser. No. 599,695, Apr. 12, 1984, Pat. No. 4,579,742.

[30] Foreign Application Priority Data

Dec. 19, 1984 [EP] European Pat. Off. ........ 84810641.5

[51] Int. Cl.$^4$ .................. A23L 2/40; A61K 9/36; A61K 9/62
[52] U.S. Cl. ..................... 426/96; 426/103; 426/302; 426/561; 426/591; 424/466; 424/496; 424/497
[58] Field of Search ................. 426/96, 561, 591, 302, 426/103; 424/33, 34, 35

[56] References Cited

U.S. PATENT DOCUMENTS

| | | | |
|---|---|---|---|
| 2,868,646 | 1/1959 | Schapiro | 426/96 |
| 3,082,091 | 3/1963 | Smith et al. | 426/591 |
| 3,667,962 | 6/1972 | Fritzberg et al. | 426/591 |
| 3,881,026 | 4/1975 | Shepherd et al. | 426/223 |
| 4,039,653 | 8/1977 | Defoney et al. | 424/19 |
| 4,579,742 | 4/1986 | Lavie | 426/96 |

FOREIGN PATENT DOCUMENTS

| | | | |
|---|---|---|---|
| A1109344 | 4/1968 | United Kingdom | 426/591 |
| A1270781 | 3/1972 | United Kingdom | 426/96 |

OTHER PUBLICATIONS

Food Technology, vol. 27, No. 11, Nov. 1973, pp. 34–44; J. A. Bakan: "Microencapsulation of Foods and Related Products".

*Primary Examiner*—Thomas G. Wiseman
*Assistant Examiner*—Elizabeth C. Weimar
*Attorney, Agent, or Firm*—Stevens, Davis, Miller & Mosher

[57] ABSTRACT

A nonhygroscopic pulverulent composition for preparing beverages with a lasting effervescence comprises a first component or group of components mixed with a second component or group of components capable of reacting mutually in the presence of water to evolve a gas. Each of said components or group of components is impregnated with the dry residue of a saccharose liquor or of a saccharose derivative liquor containing a water-soluble or a mixture of water-soluble polymers.

18 Claims, No Drawings

PULVERULENT WATER-SOLUBLE NONHYGROSCOPIC COMPOSITION FOR PREPARING BEVERAGES WITH A LASTING EFFERVESCENCE AND METHOD FOR PREPARING THE SAME

The present application is a continuation-in-part of application Ser. No. 599,695, filed on Apr. 12, 1984 now U.S. Pat. No. 4,579,742.

An object of the present invention is a pulverulent nonhygroscopic composition for preparing nutritive or nonnutritive beverages with a lasting effervescence. Another object of the invention is a method for preparing said composition.

The market for carbonated beverages and in particular for the so-called "soft drinks" or "diet drinks" is in constant expansion. This development is however hindered in the industry by the high costs associated with the transport and the handling of a product which is both heavy and bulky. Efforts are being made presently to overcome this problem by dispersing the production centers and only transporting extracts or concentrates.

In such industrial installations, the extracts or concentrates are sometimes complemented with sugar, and then completed with water and carbonated with $CO_2$ under pressure. The beverage is filled into airtight containers capable of withstanding pressure, and therefore relatively heavy and cumbersome. When the container is opened, the beverage liberates progressively its dissolved carbon dioxide, thus providing the desired sparkling effect.

Pulverulent extracts based on sodium bicarbonate and edible acids are also known which produce carbonated beverages by addition of water. However, such extracts are unable to confer to a beverage the prolonged and intense sparkling of beverages carbonated with $CO_2$ under pressure. Further, a number of ingredients amongst those necessary for conferring the desired organoleptic properties such as orthophosphoric acid, citric acid and sodium bicarbonate for example are strongly hygroscopic and therefore impair the stability of the preparations during their storage and before their use.

The chemical and the pharmaceutical industry produce and use various polymers for coating medicaments. Some of these products can be used for protecting dry extracts against the effects of humidity and to limit the possibility of the carbonates reacting with the acids. Since these products were not intended for the uses which are considered here, they have a number of shortcomings: they give a colour to the head and form deposits in the glass. Furthermore, the regularity of the $CO_2$ evolution in the beverage is most difficult to control.

The present invention overcomes the problems described above by providing a pulverulent composition where the components are effectively protected against humidity, and which once completed with water gives a carbonated beverage comparable for the intensity and the duration of its sparkling to carbonated beverages presently produced in industrial installations.

The invention is defined in the claims and primarily has for object a pulverulent water-soluble nonhygroscopic composition comprising a first component or group of components in mixture with a second component or group of components capable of mutual reaction in the presence of water to evolve a gas, each said component or group of components being impregnated with the dry residue of a saccharose liquor or of a saccharose derivative liquor containing a water-soluble or a mixture of water-soluble polymers.

Accordingly, the composition comprises as its first component or group of components a salt or a mixture of salts of carbonic acid, such as a carbonate or a bicarbonate of an alkali metal, a carbonate of an alkali earth metal, or a salt of carbonic acid and an amino acid. Preferably, the first component will be sodium bicarbonate.

The composition further comprises as its second component or group of components an acid or a mixture of acids which can be organic and/or inorganic, such as citric, tartaric, malic, ascorbic and orthophosphoric acids for example. According to the invention, each said component or group of components can further comprise natural or synthetic sweeteners such as for example: sucrose, fructose, saccharin, cyclamates and APM. Depending on the type of beverage which is to be obtained, said components can further comprise colouring agents such as a caramel colouring agent for example, essential oils or mixtures of essential oils, various extracts such as caffeine, quinine, or tolu for example, or the water-soluble extract of kola nuts. The choice of the ingredients which are included in the composition and whether they are included into the first or the second component or group of components will primarily depend on their affinity with acids or with carbonates. In fact, the only limitation imposed on the ingredients which can be included into said components or group of components is that they have to be selected from the group of products defined as being edible, and that they have to be water-soluble.

Depending on the circumstances, some of the ingredients mentioned above can be included at a later stage after the impregnation and the drying of the acids and of the carbonates according to the process of the invention.

According to the present invention, the water-soluble polymers will preferably consist of a macromolecular polysaccharide such as gum arabic or tragacanth, or of a mixture of macromolecular polysaccharides such as those mentioned. Gum arabic and tragacanth are insoluble or only partially soluble in ethanol.

According to the method of the invention, the impregnation of the components or groups of components is carried out using a saccharose liquor or a saccharose derivative liquor such as sugar caramel, further containing a selected proportion of the macromolecular polysaccharide/polysaccharides which was/were chosen.

The composition of the liquor can be advantageously modified according to the nature of the product which is to be impregnated and to the effect which is sought. In the case of the group of components comprising the acids, it suffices to provide an adequate protection against humidity and to decrease slightly the dissolution rate so as to ensure a stable pH during the reaction. As for the group of components comprising the carbonates, not only they need to be protected against humidity, but also their release should be controlled to achieve the desired duration of sparkling.

It was found that liquors based on gum arabic were particularly well suited for impregnating acids, and that liquors based on tragacanth and gum arabic can be advantageously used for impregnating carbonates. The detailed compositions of said liquors are given in the examples illustrating the invention.

These liquors, when used in accordance with the present invention, offer a number of advantages which are in particular evidenced in the finished product. The impregnation liquor used for the acids (preferably based on gum arabic) and the impregnation liquor used for the carbonates (preferably based on gum arabic and tragacanth) are both capable of agglomerating the various components of the composition, which reduces considerably the problems encountered in the dosing and packaging operations. The liquors further offer a very good support for the flavours which are included in the compositions, and they provide the desired protection against humidity, thereby improving the shelf life.

The impregnation liquor used for the protection of the acids ensures a rapid dispersion in water because of its solubility in an acidic environment, while the impregnation liquor used for the protection of the carbonates provides a controlled release of carbon dioxide over a prolonged period of time as a result of its capacity to retain the sugar coating the carbonate under the same acidic conditions.

According to the process of the invention, the impregnation of the first and of the second compound or group of compounds is carried out either by mixing the selected liquor and products under mechanical pressure, or by dissolving the selected liquor and products in a minimal amount of water. When the impregnation is carried out by mixing under mechanical pressure with a mortar or with a ball mill for example, the liquor can be diluted if desired with water to improve the impregnation of the powdered components.

Good results were obtained by using the liquor for impregnating the various components or groups of components in a proportion ranging from approximately 1.5 to 15 percent by weight of the dry powdered mixture. The group of compounds comprising the acids is generally impregnated by approximately 3 to 7% by weight of liquor, and the group comprising the carbonates by approximately 5 to 10% by weight of liquor.

When the selected ingredients are adequately impregnated, the resulting product is dried, and if desired, reduced into a powder thereafter. The drying can be carried out at moderate temperature (for example at 15°–30° C.) under a partial vacuum, at low temperature under a high vacuum, by freeze-drying, or by using a stream of warm air, for example at 50° C. The choice of the drying method will depend on the stability and on the volatility of the ingredients which are present. Also, the drying should be continued until the water content of the impregnated product is lower than a maximum of approximately 0.5 to 1% (by weight).

When necessary, the dried product can be reduced into a powder by usual methods, and stored away to be used as required.

Each of the components or group of components impregnated and dried separately is then mixed in a preselected proportion with the corresponding component or group of components. The resulting mixture is filled into appropriate containers. Such containers are preferably airtight. Although the amount of each of the products or group of products filled into the containers can vary depending on the ingredients which were used, the ratio of acids to carbonates must remain within certain limits. Typical amounts of ingredients used for a liquor of water-soluble polymer comprising approximately 100 parts by weight of an approximately 50:50 mixture of saccharose or of a saccharose derivative and of gum arabic, and approximately 64 parts by weight of an approximately 40:24 mixture of water and of ethanol. Another example of proportions of such ingredients is a liquor of water-soluble polymer comprising approximately 110 parts by weight of an approximately 60:40:10 mixture of, respectively, saccharose or saccharose derivative, gum arabic and tragacanth, and approximately 96 parts by weight of an approximately 80:16 mixture of water and of ethanol. The pulverulent compositions can be packaged as unit portions suitable for preparing by addition of water 0.3, 0.5, 1 L or more of a carbonated beverage.

Some of the embodiments of the present invention are illustrated with the following Examples. These Examples are not intended to limit in any manner the scope of the invention.

EXAMPLE 1

Pulverulent composition suitable for preparing a "kola" type beverage 1.1. Preparation of the impregnation liquor Liquor A:

10 g of sugar caramel are prepared. 40 g of water heated to 50° C. are then added to dissolve the caramel.

40 g of powdered sugar and 50 g of gum arabic are mixed together using a mortar or a blender.

The powdered sugar and the gum arabic are diluted with the warm caramel solution until a smooth lump-free product is obtained. 30 ml of 95% ethanol are then added progressively.

The resulting liquor is placed in a closed container which is then stored for 2 hours in an oven heated at 50° C.

The liquor is then perfectly smooth and ready for use.

Liquor B:

20 g of sugar caramel are prepared. 50 g of water heated to 50° C. are added to dissolve the caramel.

40 g of powdered sugar, 40 g of gum arabic and 10 g of tragacanth are mixed in their dry state using a mortar or a blender.

The powdered sugar and gums are diluted with the warm caramel solution complemented with 30 ml of warm water.

Once the product is free from any lumps, 20 ml of 95% ethanol are added progressively. The resulting liquor is placed in a closed container, which is then stored for 3 hours and 30 minutes in an oven heated at 50° C.

The liquor is then perfectly homogeneous and ready for use.

The liquors A and B are totally stable and can be stored for prolonged periods of time. Applied as a film on a glass plate, they withstand temperature variations between −20° C. and +50° C. without any alteration, and without their adhesion to the glass being modified.

1.2. Impregnation of the components (1) The following ingredients are dry-blended:

| | |
|---|---|
| 1.437 g | of powdered caramel colouring agent |
| 1.890 g | of powdered orthophosphoric acid |
| 10.720 g | of anhydrous citric acid |
| 18.900 g | of powdered tartaric acid |
| 3.000 g | of tolu extract |
| 3.000 g | of essential oils on instant sugar |
| 1.815 g | of a sweetening mixture (saccharine and cyclamates) |

-continued

| |
|---|
| 40.762 g |

This mixture is impregnated with 2 g of liquor A (5%) by homogenization in a mortar.

When the mixture is sufficiently impregnated, it is dried either under vacuum or freeze-dried as was discussed previously.

The dry product is reduced into a powder.

(2) The following ingredients are dry-blended:

| |
|---|
| 20.600 g of sodium bicarbonate |
| 0.595 g of caffeine |
| 1.437 g of a caramel colouring agent in powder |
| 22.632 g |

This mixture is impregnated with 2.26 g of liquor B (10%) by homogenization in a mortar.

When the mixture is sufficiently impregnated, it is spread in thin layers on a wire-cloth for drying in a stream of air heated to 50° C.

The dry product is reduced into a powder.

1.3. Blending of the components

The two components prepared according to the procedures 1 and 2 are filled into airtight packages containing approximately 6.34 g of dry extract each. This quantity is sufficient for preparing 300 ml of a carbonated beverage of the "kola" type. These 6.34 g are made up of 4.077 g of the components of the acid group, and 2.264 g of the components of the second group.

EXAMPLE 2

Pulverulent composition suitable for preparing a "kola" type beverage

The following ingredients are dissolved in water:

| |
|---|
| 1.00 g of a caramel colouring agent |
| 60.00 g of powdered caramel containing 0.71 g of orthophosphoric acid (Swiss Patent N° 625228) |
| 11.00 g of anhydrous citric acid |
| 19.00 g of powdered tartaric acid |
| 3.00 g of tolu extract on instant sugar |
| 3.00 g of essential oils on instant sugar |
| 1.80 g of a sweetening mixture (saccharine and cyclamates) |
| 6.00 g of a water-soluble extract of kola nuts |
| 104.80 g |

The dissolution was carried out using enough water to obtain a solution with a sufficient fluidity to be filtered if necessary.

3.14 g (3%) of liquor A (Example 1) are added to this solution. The mixture is made homogeneous by stirring, and then freeze-dried.

The dehydrated mixture is reduced into a powder.

This mixture is complemented with the corresponding amount of bicarbonate impregnated with the liquor B, and used as in Example 1 for preparing a carbonated beverage of the "kola" type.

The "acid" dry extracts prepared according to the methods described in Example 1 and 2 can also be used for preparing "kola" type beverages in drinking fountains. In these apparatuses, the carbonation is ensured by the use of $CO_2$ under pressure, and the amount of acid can be reduced by the amount which is necessary for neutralizing the bicarbonate.

EXAMPLE 3

Pulverulent composition for preparing a cabonated limeade (1) The following ingredients are dry-blended:

| |
|---|
| 1.89 g of orthophosphoric acid |
| 10.72 g of anhydrous citric acid |
| 18.90 g of powdered tartaric acid |
| 3.00 g of a sweetening mixture (saccharine and cyclamates) |
| 3.00 g of tolu extract |
| 3.00 g of essential oil of lime on instant sugar |
| 40.51 g |

This mixture is impregnated with 2.30 g (6%) of liquor A (prepared as described in Example 1). When the mixture is sufficiently impregnated, it is dried under vacuum at 30° C.

After drying, the product is reduced into a powder.

(2) 20.60 g of sodium bicarbonate are impregnated with 2 g (10%) of liquor B (prepared as described in Example 1).

This product is dried in a stream of air heated to 50° C.

The two components prepared according to the procedures 1 and 2 are mixed in an adequate proportion and filled into airtight packages. The quantities given in this Example are sufficient for preparing 3 L of limeade.

EXAMPLE 4

Pulverulent composition for "bitter" type carbonated beverages (1) The following ingredients are dry-blended:

| |
|---|
| 1.89 g of powdered orthophosphoric acid |
| 10.00 g of anhydrous citric acid |
| 20.00 g of powdered tartaric acid |
| 2.40 g of a sweetening mixture (saccharine and cyclamates) |
| 0.0015 g of quinine chlorhydrate |
| 34.2915 g |

This mixture is impregnated with 1.80 g (approximately 6%) of liquor A (prepared as described in Example 1) complemented with 0.30 g of essential oil of lemon on instant sugar.

The drying is carried out at 30° C. and under a partial vacuum.

The dried product is reduced into a powder.

(2) 20.06 g of sodium bicarbonate are impregnated with 2.00 g (approximately 10%) of liquor B (prepared as described in Example 1).

This product is dried in a stream of air heated to 50° C.

The dried product is reduced into a powder.

The two components prepared according to the procedures 1 and 2 are mixed together to produce a composition sufficient for preparing 3 L of a "bitter" type lemonade.

What is claimed is:

1. A pulverulent effervescent, water-soluble, non-hygroscopic composition for use as the basis for diet or soft drinks, said composition comprising a mixture of components in particulate form capable of reacting mutually in the presence of water to evolve gas, characterized in that each of the particulate components is impregnated with the dry residue of a heat-treated saccharose or saccharose derivative ethanolic liquor containing gum arabic.

2. A composition according to claim 1, wherein the heat treated ethanolic liquor has been subjected to a thermal treatment in an airtight container heated to a temperature of about 50° C.

3. A composition according to any one of claims 1 and 2, wherein a first component of the mixture comprises a salt or a mixture of salts of carbonic acid and wherein a second component of the mixture comprises an acid or a mixture of organic and/or inorganic acids.

4. A composition according to claim 3, wherein the acid or acids is selected from the group consisting of citric, tartaric, malic, ascorbic and orthophosphoric acid and mixtures thereof and wherein the salt is selected from the group consisting of a carbonate or a bicarbonate of an alkali metal, a carbonate of an alkali earth metal, and the salt of carbonic acid and an amino acid.

5. A composition according to claim 1, wherein at least one component of the mixture contains at least one member selected from the group consisting of sweeteners, colouring agents, and flavouring agents.

6. A composition according to claim 1, wherein the ethanolic liquor includes tragacanth gum.

7. A method for preparing a pulverulent effervescent, water-soluble, non-hygroscopic composition for use as the basis of diet or soft drinks, said composition containing a mixture of components in particulate form capable of reacting mutually in the presence of water to evolve gas, which comprises
   (a) preparing a solution of saccharose or saccharose derivative in water containing a macromolecular polysaccharide or mixture of macromolecular polysaccharides which are water-soluble but insoluble or only partially soluble in ethyl alcohol;
   (b) adding ethyl alcohol to the above solution while stirring, to form a liquor;
   (c) storing the thus obtained liquor in an airtight container at a temperature of about 50° C.;
   (d) separately impregnating or coating the particles of each of said components with the liquor resulting from step (c) above;
   (e) separately drying the thus impregnated or coated particles; and
   (f) mixing together the dried impregnated or coated particles in the desired proportions.

8. Method according to claim 7, wherein the liquor of water-soluble macromolecular polysaccharides resulting from step (c) comprises approximately 100 parts by weight of an approximately 50:50 mixture of saccharose or of a saccharose derivative and of gum arabic, and approximately 64 parts by weight of an approximately 40:24 mixture of water and of ethyl alcohol.

9. Method according to claim 7, wherein the liquor of water-soluble macromolecular polysaccharides resulting from step (c) comprises approximately 110 parts by weight of an approximately 60:40:10 mixture of, respectively, saccharose or a saccharose derivative, gum arabic and tragacanth gum, and approximately 96 parts by weight of an approximately 80:16 mixture of water and of ethyl alcohol.

10. Method according to claim 7, wherein the composition comprises a mixture of two components.

11. A method according to claim 7, wherein at least one of the components itself comprises a mixture of at least two members, one member selected from the group consisting of a salt of carbonic acid, an organic acid and an inorganic acid, and at least one member selected from the group consisting of a sweetener, a coloring agent, an essential oil, and an extract of caffeine, of quinine, of tolu balsam or of cola nuts.

12. Method according to claim 7, wherein the impregnation or coating or particles is carried out by mixing the particles of selected components with the liquor under mechanical pressure.

13. Method according to claim 7, wherein at least one of the selected components is impregnated by dissolving the selected components and the liquor in water.

14. Method according to claim 13, wherein the thus impregnated component is reduced to particulate form, after drying.

15. Method according to claim 7, wherein the saccharose derivative is a mixture of sugar and caramel of sugar.

16. Method according to claim 7, wherein the particles of components comprise particles of a salt or a mixture of salts of carbonic acid and particles of mineral acid and/or an organic acid.

17. Method according to claim 16, wherein the salt of carbonic acid is an alkaline carbonate or bicarbonate or an alkaline earth carbonate or a salt of carbonic acid and an amino acid.

18. Method according to claim 16, wherein the organic acid is citric and/or tartaric acid, and the mineral acid is orthophosphoric acid.

* * * * *